US00PP27968P3

(12) United States Plant Patent
Van Paemel

(10) Patent No.: US PP27,968 P3
(45) Date of Patent: May 2, 2017

(54) ***HELLEBORUS* PLANT NAMED 'JHE00091'**

(50) Latin Name: *Helleborus×hybridus*
Varietal Denomination: JHE00091

(71) Applicant: Thierry Van Paemel, Oostkamp (BE)

(72) Inventor: Thierry Van Paemel, Oostkamp (BE)

(73) Assignee: Floreac N.V. div Microflor, Lochristi (BE)

( * ) Notice: Subject to any disclaimer, the term of this patent is extended or adjusted under 35 U.S.C. 154(b) by 24 days.

(21) Appl. No.: 14/756,541

(22) Filed: Sep. 15, 2015

(65) Prior Publication Data

US 2017/0079184 P1 Mar. 16, 2017

(51) Int. Cl.
*A01H 5/02* (2006.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'JHE00091', characterized by its upright and mounding plant habit; vigorous growth habit and rapid growth rate; dark green-colored leaves; early and freely flowering habit; single purple-colored flowers; and good garden performance.

2 Drawing Sheets

Botanical designation: *Helleborus×hybridus*.
Cultivar denomination: 'JHE00091'.

BACKGROUND OF THE INVENTION

The present invention relates to a new and distinct cultivar of *Helleborus* plant, botanically known as *Helleborus×hybridus* and hereinafter referred to by the name 'JHE00091'.

The new *Helleborus* plant is a product of a planned breeding program conducted by the Inventor in Oostkamp, Belgium. The objective of the breeding program was to create new early-flowering *Helleborus* plants with attractive plant habit and flowers.

The new *Helleborus* plant originated from a cross-pollination conducted by the Inventor in Oostkamp, Belgium in 2007 of a proprietary selection of *Helleborus×hybridus* identified as code designation OERODE1209, not patented, as the female, or seed, parent with a proprietary selection of *Helleborus×hybridus* identified as code designation OERODE1205, not patented, as the male, or pollen, parent. The new *Helleborus* plant was discovered and selected by the Inventor as a single flowering plant from within the progeny of the stated cross-pollination grown in a controlled greenhouse environment in Oostkamp, Belgium in March, 2009.

Asexual reproduction of the new *Helleborus* plant by in vitro propagation in a controlled environment in Lochristi, Belgium since June, 2011 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'JHE00091'. These characteristics in combination distinguish 'JHE00091' as a new and distinct *Helleborus* plant:

1. Upright and mounding plant habit.
2. Vigorous growth habit and rapid growth rate.
3. Dark green-colored leaves.
4. Early and freely flowering habit.
5. Single purple-colored flowers.
6. Good garden performance.

Compared to plants of the parent selections, plants of the new *Helleborus* are more vigorous and grow faster. In addition, plants of the new *Helleborus* flower earlier than plants of the female parent selection.

Plants of the new *Helleborus* can be compared to plants of *Helleborus orientalis* 'HLR 120', disclosed in U.S. Plant Pat. No. 21,503. In side-by-side comparisons conducted in Oostkamp, Belgium, plants of the new *Helleborus* differed primarily from plants of 'HLR 120' in the following characteristics:

1. Plants of the new *Helleborus* flowered earlier than plants of plants of 'HLR 120'.
2. Plants of the new *Helleborus* were more freely flowering than plants of 'HLR 120'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'JHE00091' grown in a container.

The photograph on the second sheet is a close-up view of a typical flower of 'JHE00091'.

DETAILED BOTANICAL DESCRIPTION

The aforementioned photographs and following observations, measurements and values describe plants grown during the autumn in 17-cm containers in a glass-covered greenhouse in Lochristi, Belgium and under cultural practices typical of commercial *Helleborus* production. During the production of the plants, day temperatures ranged from 5° C. to 26° C. and night temperatures ranged from 5° C. to 18° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus×hybridus* 'JHE00091'.

Parentage:

*Female, or seed, parent*.—Proprietary selection of *Helleborus×hybridus* identified as code designation OERODE1209, not patented.

*Male, or pollen, parent*.—Proprietary selection of *Helleborus×hybridus* identified as code designation OERODE1205, not patented.

PROPAGATION:

*Type*.—By in vitro propagation.

*Time to initiate roots, summer*.—About six weeks at temperatures about 19° C.

*Time to produce a rooted young plant, summer*.—About seven months at temperatures about 19° C.

*Root description*.—Medium in thickness, fleshy; typically white to brown in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial; upright and mounding plant habit with flowers held above the foliar plane; plant shape is roughly globular; vigorous growth habit and rapid growth rate.

*Plant height, soil level to top of foliar plane*.—About 24.5 cm.

*Plant height, soil level to top of floral plane*.—About 38 cm.

*Plant diameter* (*area of spread*).—About 42.3 cm.

Leaf description:

*Arrangement*.—Leaves arranged in a basal rosette; leaves palmately compound with five leaflets per leaf.

*Leaf length*.—About 15.9 cm.

*Leaf width*.—About 23 cm.

*Leaflet length*.—About 14.2 cm.

*Leaflet width*.—About 4.2 cm.

*Leaf shape*.—Palmate; reniform in outline.

*Leaflet shape*.—Narrowly obovate.

*Leaflet apex*.—Acute.

*Leaflet base*.—Attenuate.

*Leaflet margin*.—Serrate.

*Leaflet texture, upper and lower surfaces*.—Smooth, glabrous; slightly rugose.

*Leaflet luster, upper surface*.—Glossy.

*Leaflet luster, lower surface*.—Slightly glossy.

*Leaflet venation pattern*.—Pinnate.

*Leaflet color*.—Developing leaves, upper surface: Close to 143A to 143B. Developing leaves, lower surface: Close to 144A. Fully developed leaves, upper surface: Close to darker than between NN137A and 147A; venation, close to 144A. Fully developed leaves, lower surface: Close to 147B; venation, close to 144B to 144C.

*Petioles*.—Length: About 15.2 cm. Diameter: About 3.5 mm. Texture, upper and lower surfaces: Smooth, glabrous. Luster, upper and lower surfaces: Glossy. Color, upper and lower surfaces: Close to 144A.

Flower description:

*Flower shape and habit*.—Single rotate flowers in terminal compound cymes; freely and uniform flowering habit with about 28 flower buds and flowers per plant; flowers facing outwardly to nodding.

*Fragrance*.—None detected.

*Natural flowering season*.—Plants begin flowering about ten months after planting; plants flower during the autumn and winter in Belgium.

*Flower longevity on the plant*.—About ten days; flower longevity is dependent on temperature; flowers not persistent.

*Inflorescence height*.—About 15.9 cm.

*Inflorescence diameter*.—About 36.6 cm.

*Flower buds*.—Length: About 1.4 cm. Diameter: About 1.1 cm. Shape: Short oblong. Texture: Glabrous. Luster: Matte. Color: Close to between N77B and 183B.

*Flower diameter*.—About 5.3 cm.

*Flower depth* (*height*).—About 1.6 cm.

*Petals*.—Transformed into nectaries.

*Sepals*.—Quantity and arrangement: Five, arranged in a single whorl. Length: About 3.2 cm. Width: About 2.5 cm. Shape: Broadly obovate. Apex: Obtuse to shallowly retuse. Base: Cuneate. Margin: Entire. Texture, upper and lower surfaces: Smooth, glabrous. Luster, upper and lower surfaces: Matte. Color: When opening, upper surface: Close to 187B; dense venation, close to N186A. When opening, lower surface: Close to N77B; dense venation, close to N186A. Fully opened, upper and lower surfaces: Close to N77B; dense venation, close to N186A.

*Peduncles*.—Length: About 19.8 cm. Diameter: About 5 mm. Aspect: About 30° from vertical. Strength: Moderately strong. Texture: Smooth, glabrous. Luster: Slightly glossy. Color: Close to between 144A and 144B.

*Pedicels*.—Length: About 2.6 cm. Diameter: About 1.5 mm. Aspect: About 20° from peduncle axis. Strength: Moderately strong. Texture: Smooth, glabrous. Luster: Glossy. Color: Close to 146D; distally, tinged with close to 184B to 184C.

*Reproductive organs*.—Stamens: Quantity per flower: About 60. Filament length: About 1.1 cm. Filament color: Close to 145D. Anther shape: Reniform; basifixed. Anther size: About 2 mm by 1.25 mm. Anther color: Close to 150D. Pollen amount: Scarce. Pollen color: Close to 155A. Pistils: Quantity per flower: About four. Pistil length: About 8 mm. Stigma diameter: About 3 mm. Stigma shape: Club-shaped. Stigma color: Close to 145D. Style length: About 7.5 mm. Style color: Close to 145B strongly tinged with close to 183C to 183D. Ovary color: Close to 145B. Nectaries (transformed petals): Quantity per flower: About 13. Length: About 6 mm. Diameter: About 4 mm. Shape: Tubular, flattened. Texture, inner and outer surfaces: Smooth, glabrous. Luster, inner surface: Matte. Luster, outer surface: Glossy. Color, immature and mature, inner surface: Close to N144A; distally, strongly tinged with close to 200D. Color, immature and mature, outer surface: Close to 146C; distally, tinged with close to 197A.

*Seeds and fruits*.—Seed and fruit development have not been observed on plants of the new *Helleborus*.

Garden performance: Plants of the new *Helleborus* have been observed to have good garden performance and to tolerate rain, wind and high temperatures about 35° C. and to be suitable for USDA Hardiness Zones 5 to 9.

Pathogen & pest resistance: Plants of the new *Helleborus* have not been observed to be resistant to pathogens and pests common to *Helleborus* plants.

It is claimed:

1. A new and distinct *Helleborus* plant named 'JHE00091' as illustrated and described.

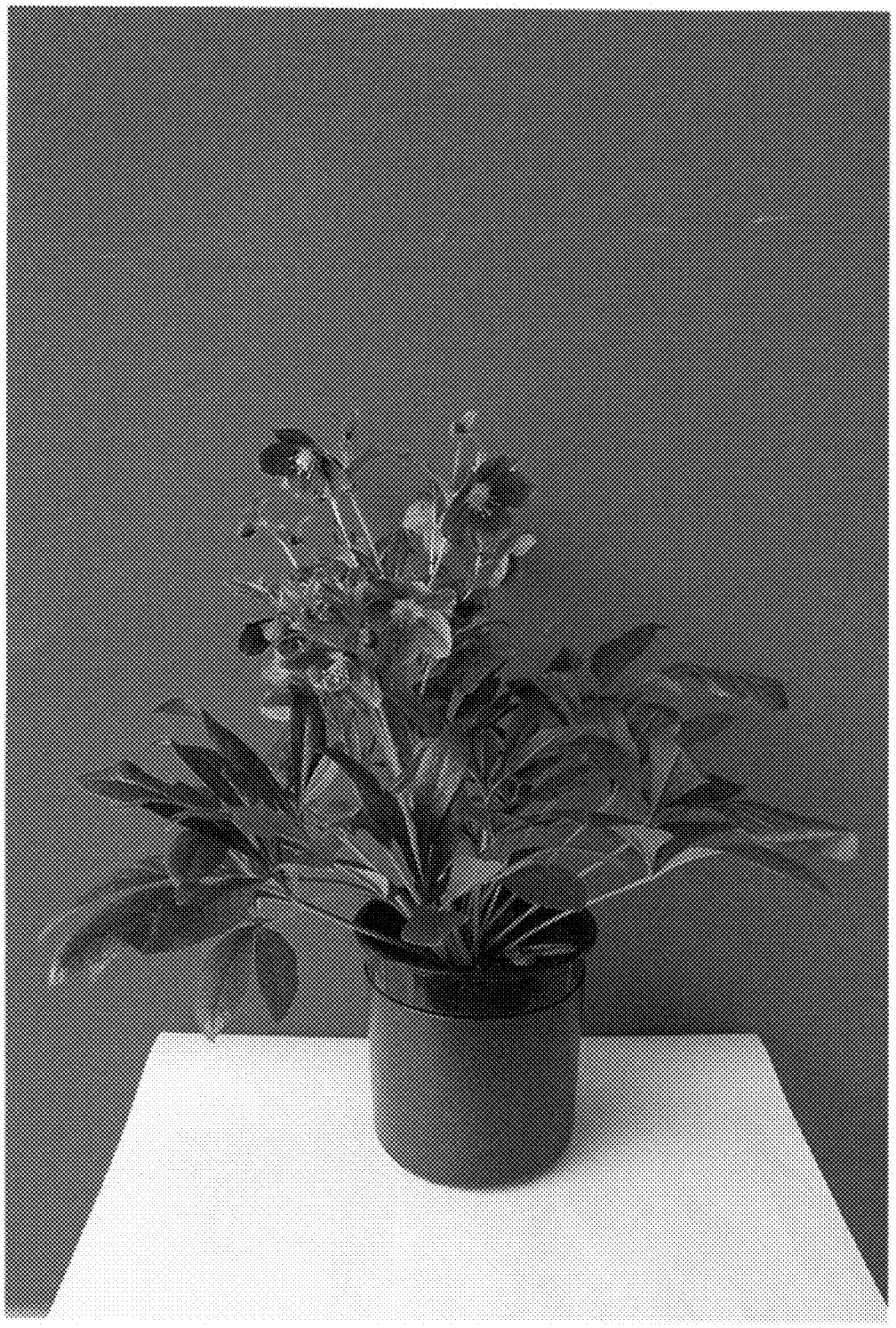

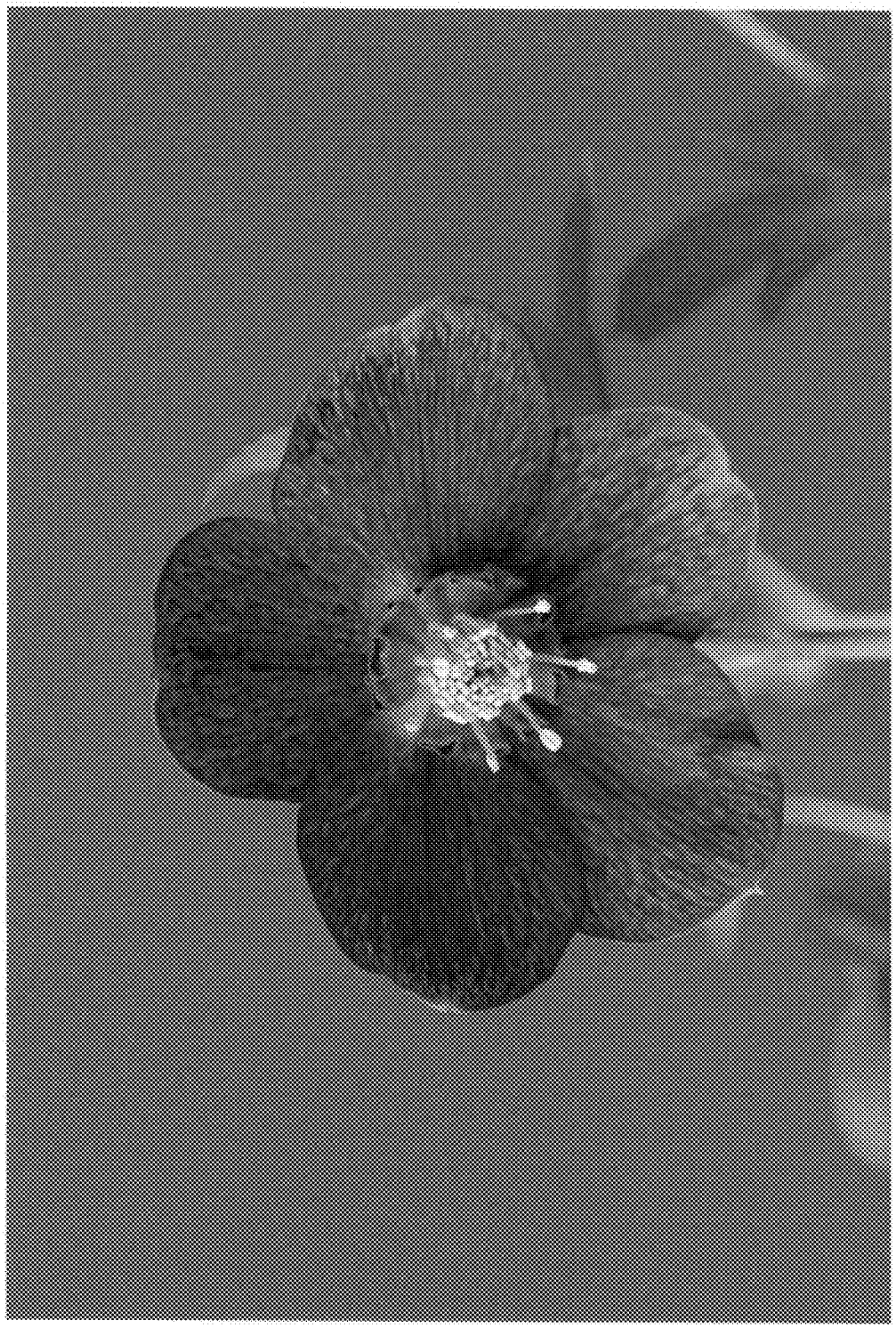

* * * * *